United States Patent [19]

Sos et al.

[11] Patent Number: 5,122,121
[45] Date of Patent: Jun. 16, 1992

[54] SAFETY NEEDLE ASSEMBLY

[75] Inventors: Thomas A. Sos, New Rochelle; Eamonn Hobbs, Queensbury, both of N.Y.

[73] Assignee: E-Z-EM, Inc., Westbury, N.Y.

[21] Appl. No.: 575,436

[22] Filed: Aug. 30, 1990

[51] Int. Cl.⁵ .......................................... A61M 5/178
[52] U.S. Cl. .................................. 604/167; 604/169; 604/274; 604/408
[58] Field of Search ............. 604/52, 83, 86, 158-163, 604/167, 169, 240, 256, 257, 262, 272, 283, 408, 411, 412, 274, 164

[56] References Cited

U.S. PATENT DOCUMENTS

| | | | |
|---|---|---|---|
| 2,346,334 | 4/1944 | Shaw | 604/86 |
| 2,564,977 | 8/1951 | Hu | 604/272 X |
| 3,406,685 | 10/1968 | May | 604/164 |
| 3,474,786 | 10/1969 | Spademan | 604/163 |
| 3,757,771 | 9/1973 | Ruegg et al. | 604/163 X |
| 4,504,265 | 3/1985 | Rudzena et al. | 604/86 |
| 4,513,754 | 4/1985 | Lee | 128/753 |
| 4,700,694 | 10/1987 | Shishido | 128/6 |
| 4,808,157 | 2/1989 | Coombs | 604/44 |
| 4,838,875 | 6/1989 | Somor | 604/262 |
| 4,935,008 | 6/1990 | Lewis, Jr. | 604/52 |
| 4,998,977 | 3/1991 | Preiss et al. | 128/673 |
| 5,000,740 | 3/1991 | Ducharme et al. | 604/162 |
| 5,000,745 | 3/1991 | Guest et al. | 604/256 |
| 5,046,509 | 9/1991 | Kater | 128/764 |

FOREIGN PATENT DOCUMENTS 0418525 9/1925 Fed. Rep. of Germany.

Primary Examiner—John D. Yasko
Assistant Examiner—Adam J. Cermak
Attorney, Agent, or Firm—McAulay Fisher Nissen Goldberg & Kiel

[57] ABSTRACT

A safety needle for use in the vascular system. The needle has a first end adapted to be placed in the vascular system and a second end with a stopper and adapted to pass a guide wire. The needle has a port positioned between the first and second needle ends. The port is adapted to be connected to a blood collection device. The blood which enters the first end of the needle is diverted through the port to the blood collection device which avoids having the blood reach the second end of the needle.

16 Claims, 2 Drawing Sheets

SAFETY NEEDLE ASSEMBLY

BACKGROUND OF THE INVENTION

The present invention relates to a safety needle assembly and more particularly to a needle assembly which can be used during angiographic procedures.

Angiographic procedures are initiated by a needle puncture into an artery, typically the femoral artery, in the groin area. The needle puncture technique is called the Seldinger Technique and it can be performed using either a one or two piece needle. In the procedure, the sharpened part of the needle is inserted through the skin into the artery lumen. Blood is observed exiting the needle to insure that the needle has been properly placed. The technique may also involve test injection of contrast medium to insure the proper placement of the needle.

Physicians, or other health professionals working with a patient during angiographic procedures, often come in contact with the arterial blood that spurts from the needle during the initial needle puncture. This contact with blood increases the likelihood of contracting an infectious disease. With the advent of AIDS and the increase in hepatitis it becomes of greater importance to prevent inadvertent contact with blood.

There are a number of devices known in the prior art which connect to catheters to reduce blood loss during an angiographic procedure. These devices are called hemostasis devices. These hemostasis devices do not attach to needles and are not intended to protect a physician from blood contact during the initial needle stick A safe stick adaptor is known in the prior art to protect a physician from blood contact during the initial needle puncture. This adaptor is marketed by Cook Incorporated of Bloomington, Ind. The Cook adaptor is bulky and relies upon manually fixing a Tuohy-Borst valve around a wire guide inserter. The Cook adaptor is locked onto an access needle with a wire guide prepositioned through the Tuohy-Borst valve prior to puncture. The pulsatile artery blood which flashes back during the initial needle puncture is contained in a sidearm plastic sheath. After this is done the Tuohy-Borst valve is loosened so that a guide wire can be advanced. Use of this device is cumbersome, time consuming and excessive loosening of the Tuohy-Borst valve may cause blood to spurt from the device.

It is accordingly an objective of the present invention to provide a safety needle assembly which is easy to use and which protects the physician, or other health professional, from contact with blood during the initial needle puncture of an angiographic procedure.

BRIEF DESCRIPTION

The present invention relates to safety needle assembly. The needle assembly includes an elongated needle having a sharpened end for introduction into an arterial lumen. The elongated needle has a second, hub end through which a guide wire can be passed. The hub end of the needle is formed with a port therein. The port can be connected to a blood collection device so that blood which enters into the needle is diverted through the port into the blood collection device. The hub end of the needle is also provided with a stopper. The stopper is designed such that a guidewire can be passed therethrough. However, even with the guidewire positioned through the stopper, the stopper provides an effective barrier to fluid flow. In combination the diverting port and the stopper prevent arterial blood, under pressure, from spurting out of the hub end of the needle.

DETAILED DESCRIPTION OF THE PREFERRED EMBODIMENT

Figure 1:
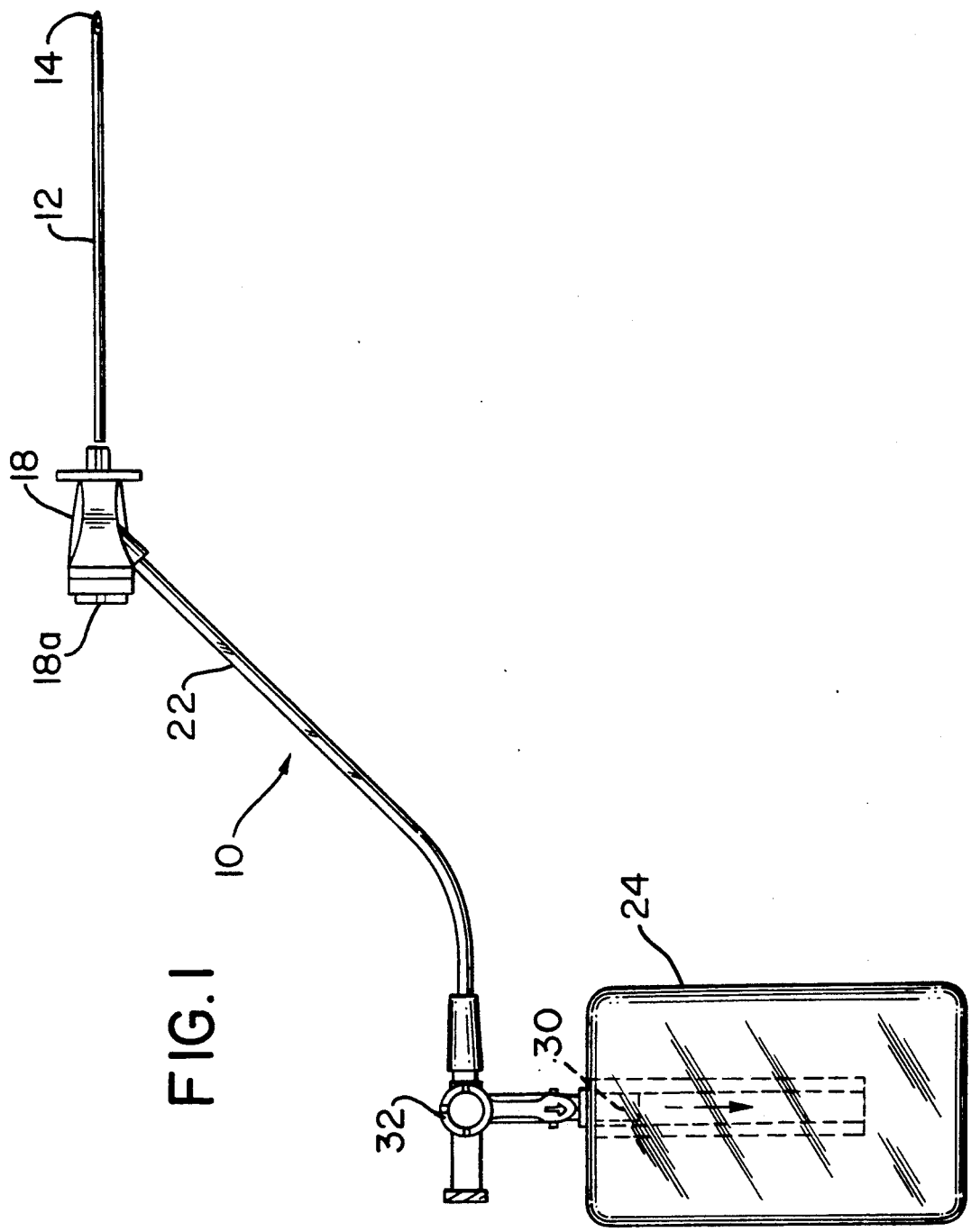
FIG. 1 is a perspective view of one embodiment of the safety needle assembly of the present invention showing the needle and collection bag.
Figures 2, 3:
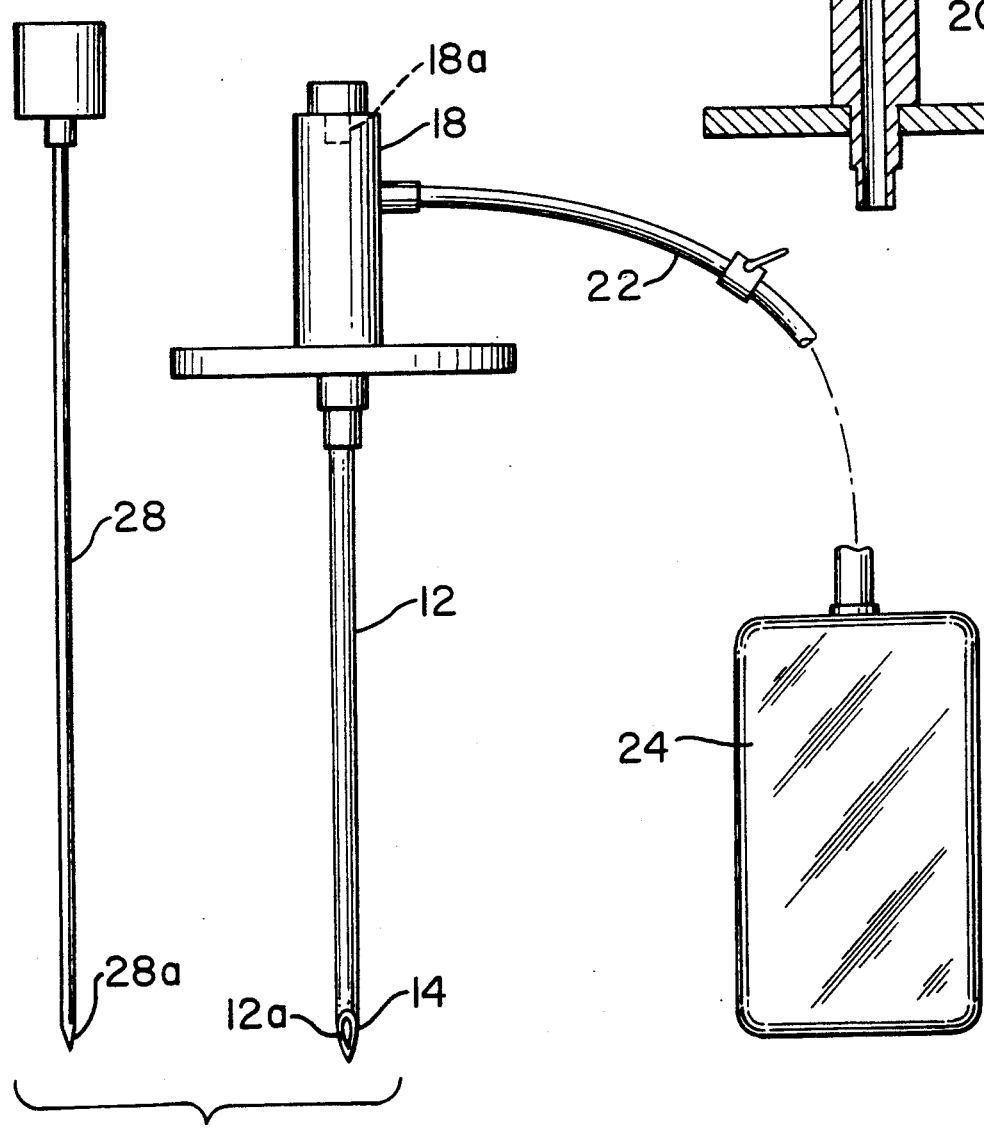
FIG. 2 is a view showing an alternative embodiment of the invention showing a two piece needle.
FIG. 3 is a sectional view of the hub portion of the FIG. 1 needle.

Referring now to the drawings the reference numeral 10 general denotes the needle assembly of the present invention. Needle assembly 10 includes a needle body 12. Needle body 12 has a first end 14 which is shaped and dimensioned for introduction into the arterial lumen of an animal and a second, hub end 18. Needle assembly 10 may also be used for introduction of the needle body into a venous lumen.

Hub end 18 of needle body 12 is formed with a port 20 therein. Port 20 is adapted for connection to a tube 22. Tube 22 is adapted for connection to blood collecting bag 24.

Hub end 18 of the needle body 12 is provided with a stopper 26 which in the preferred embodiment of the invention is a rubber diaphram disc. A guide wire (not shown) can be passed through stopper 26 into needle body 12. The guide wire is passed through opening 18a of the hub end. When a guide wire is passed through the stopper 26 the stopper still provides a barrier to the flow of blood. Thus blood which enters into needle body 12, under pressure, cannot exit from second, hub end 18.

In a preferred embodiment of the invention both tube 22 and the blood collecting bag 24 may be formed of either silicone or polyvinylchloride. Both tube 22 and blood collecting bag 24 are formed of a material that will enable a user to see blood therethrough. Tube 22 is preferably formed of a material that is sufficiently pliable to allow a user to feel an arterial pulse therethrough, although less pliable materials may be used. The material from which the tube 22 and the bag 24 are made enable a physician to obtain necessary data to determine if the needle is properly placed.

Needle assembly 10 may be used with a stylet 28. Although any stylet and needle combination may be used together, in a preferred embodiment, stylet 28 and needle body 12 have matched bevels 28a, 12a and shapes.

Blood collecting bag 24 is provided with a one way valve 30 to prevent blood from flowing outwardly from the bag. In the preferred embodiment of the invention valve 30 is a reed valve. A three way stopcock 32 is provided. One port of stopcock 32 is attached to tube 22. A second port of stockcock 32 connects to bag 24. A third port of stopcock 32 is adapted to connect to a syringe. By having the stopcock connectable to a syringe a user can test inject contrast medium into the patient to ascertain the position of the needle body 12.

In use needle assembly 10 provides an inexpensive and safe means to protect the operator and personnel from inadvertent contact with blood during the initial needle puncture of an angiographic procedure. After the needle is placed in the arterial lumen, blood exits through port 20 into tube 22, rather than having the blood exit from the hub end 18 of the needle as it did in prior art devices. The physician is still able to visualize the blood flow and determine to if the blood is pulsatile or non-pulsatile. Further, the operator is able to perform test injections of contrast medium through the needle without having to attach a syringe directly to the needle or through a tube which is necessary in prior art devices. This eliminates possible dislodgement of the needle from the lumen of the vessel which occurred, at times, with the prior art methods.

What is claimed:

1. A needle assembly useable with a guide wire in the vascular system comprising:

an elongated needle having a first end shaped and dimensioned for introduction into the vascular system and a second end capable of receiving a guide wire therethrough, said needle having a port positioned between said first and second ends;

stopper means for sealing said second end, said stopper means being formed such that a guide wire may be passed therethrough said stopper means preventing blood flow outwardly from said second needle end;

a tube having a first end and a second end, said tube connectable at its first end to said needle port; and a bag connectable to said second end of said tube whereby blood entering said first needle end flow through said port into said bag thus preventing said blood form flowing to said second needle end.

2. The needle assembly of claim 1 wherein said needle includes a hub segment and wherein said port and said stopper means are positioned in said hub segment.

3. The needle assembly of claim 2 wherein said hub segment has a larger inner and outer diameter than said needle.

4. The needle assembly of claim 2 wherein said hub segment is formed separately from the rest of said elongated needle.

5. The needle assembly of claim 1 wherein said stopper means is a rubber diaphragm disc.

6. The needle assembly of claim 1 and further including a stylet shaped and dimensioned to be received in said needle.

7. The needle assembly of claim 1 wherein said tube is sufficiently pliable to enable an arterial pulse to be felt therethrough.

8. The needle assembly of claim 1 wherein said tube is sufficiently transparent to permit blood to be seen therein.

9. The needle assembly of claim 1 wherein said bag is sufficiently transparent to permit blood to be seen therein.

10. The needle assembly of claim 9 wherein said hub segment is formed separately from the rest of said elongated needle.

11. The needle assembly of claim 1 wherein said tube and said bag are formed of silicone.

12. The needle assembly of claim 1 wherein said tube and said bag are formed of polyvinyl chloride.

13. The needle assembly of claim 1 and further including a blood collection device connected to said needle port, said blood collection device includes a one-way valve to prevent blood from exiting from said device.

14. The needle assembly of claim 1 wherein said bag includes a one-way valve to prevent blood from exiting therefrom.

15. The needle assembly of claim 1 and further including a three way stopcock having a first port connectable to said bag, a second port connectable to said tube, and a third port adapted for connection to a syringe to enable the use of test injections of contrast media.

16. The needle assembly of claim 1 further including a stylet wherein said stylet and said needle first end are both beveled and wherein said stylet and said needle first end are both formed such that when said stylet is fully advanced in said needle the beveled ends of said stylet and needle align to form a single oblique plane relative to a common annular axis of the stylet and needle.

* * * * *